US006123936A

United States Patent [19]

Platz et al.

[11] Patent Number: 6,123,936
[45] Date of Patent: Sep. 26, 2000

[54] METHODS AND COMPOSITIONS FOR THE DRY POWDER FORMULATION OF INTERFERONS

[75] Inventors: Robert M. Platz, Half Moon Bay, Calif.; Shigenobu Kimura, Hyogo; Yu-ichiro Satoh, Sapporo, both of Japan; Linda C. Foster, Mountain View, Calif.

[73] Assignee: Inhale Therapeutics Systems, Inc., San Carlos, Calif.

[21] Appl. No.: 09/444,116

[22] Filed: Nov. 22, 1999

Related U.S. Application Data

[63] Continuation of application No. 08/737,724, filed as application No. PCT/US95/06008, May 15, 1995, which is a continuation-in-part of application No. 08/246,034, May 18, 1994, abandoned.

[51] Int. Cl.$^7$ .............................. A61K 38/21; C07K 1/36

[52] U.S. Cl. ............................. 424/85.6; 530/351; 514/2; 435/70.1; 424/43; 424/46; 424/489; 424/491

[58] Field of Search .................................. 424/85.6, 85.4, 424/43, 46, 489, 491; 530/351, 363; 514/2, 21; 435/70.1; 128/200.14, 200.33

[56] References Cited

U.S. PATENT DOCUMENTS 5,049,389 9/1991 Radhakrishnan ........................ 424/450

FOREIGN PATENT DOCUMENTS

WO91/16038 10/1991 WIPO .
WO93/00951 1/1993 WIPO .

*Primary Examiner*—David Guzo
*Assistant Examiner*—Jon Shuman
*Attorney, Agent, or Firm*—Susan T. Evans; Felissa H. Cagan; Stephen L. Burst

[57] ABSTRACT

According to the present invention, methods and compositions are provided for spray-dried, interferon-based dry powder compositions, particularly interferon-beta. The compositions are useful for treating conditions in humans that are responsive to treatment with interferons. In particular, the methods of the present invention rely on spray drying to produce stable, high-potency dry powder formulations of interferons, including but not limited to IFN-beta. Surprisingly, it has been found that IFN can be prepared in high potency, dry powder formulations by spray drying. Such dry powder formulations find particular utility in the pulmonary delivery of IFN.

22 Claims, No Drawings

METHODS AND COMPOSITIONS FOR THE DRY POWDER FORMULATION OF INTERFERONS

CROSS-REFERENCE TO RELATED APPLICATIONS

This application is a Continuation of U.S. patent application Ser. No. 08/737,724, filed on Jul. 14, 1997, which is a 371 of PCT/US95/06008, filed May 15, 1995, which is a continuation-in-part of U.S. patent application Ser. No. 08/246,034, filed May 18, 1994 now abandoned.

BACKGROUND OF THE INVENTION

1. Field of the Invention

The present invention relates generally to methods and compositions for the dry powder formulation of cytokines, especially interferons. More particularly, the present invention relates to the spray drying of interferons (IFNs) to produce dry powder formulations of high potency.

2. Description of the Background Art

Interferons are cytokines useful in the treatment of a variety of human diseases ranging from cancer to immune system enhancement. Interferons are commonly formulated as isotonic aqueous solutions for parenteral administration. Recently, clinicians have sought alternative routes of administration for interferons more suitable to long term use by patients. Particularly, aerosol formulations of interferons have been produced for pulmonary delivery as described in WO 91/16038. The formulation is dispersed by volatilization of a liquid propellent. The patent teaches adding a surfactant or the like to improve the dispersibility of a human interferon from a freon delivery system.

Methods and compositions for the preparation of solid polypeptide microparticles as a pharmaceutical aerosol formulation are disclosed in WO 91/16038 wherein IFN-beta was prepared in dry powder form by lyophilizing an aqueous solution of IFN and jet milling following lyophilization. The purification of proteins of molecular weight in excess of 12,000, including human IFN is disclosed in U.S. Pat. No. 4,503,035. Low pH pharmaceutical compositions of recombinant IFN-beta are disclosed in WO 89/05158.

Because interferons are fairly expensive compounds, it is highly desirable to have formulations of high potency with improved flow characteristics that can be used with high efficiency in dry powder inhalers to produce reproducible doses for pulmonary delivery.

An object of the present invention is to provide an interferon-containing composition suitable for long-term pulmonary administration to a patient in need thereof. Another object of this invention is to provide an interferon-containing powdered composition that is administered by inhalation in a manner that is free of a liquid propellant such as a FREON or carbon dioxide.

Another object of this invention is to provide an interferon-containing powdered composition that can be easily manufactured by a method that maintains a high percentage of interferon activity.

Still another object of this invention is to provide an interferon-containing composition that exhibits a high level of stability of the interferon over time.

Other objects may be apparent to one of ordinary skill upon reviewing the following specification and claims.

SUMMARY OF THE INVENTION

One aspect of this invention is an interferon-based dry powder composition for pulmonary delivery, said composition comprising a therapeutically effective amount of interferon in combination with a pharmaceutically acceptable carrier.

Another aspect of this invention is a unit dosage form for pulmonary delivery of interferon, which dosage form comprises a unit receptacle containing the interferon-based dry powder composition of this invention.

A third aspect of this invention is a method of treating a disease state responsive to treatment by interferon, which method comprises administering a physiologically effective amount of the interferon-based dry powder composition to the pulmonary region of the lung of a subject in need thereof.

Still another aspect of this invention is a method for aerosolizing the interferon-based dry powder composition that comprise dispersing an amount of the dry powder composition in a gas stream to form an aerosol and capturing the aerosol in a chamber having a mouthpiece for subsequent inhalation by a patient.

Still another aspect of this invention is a method for preparing the interferon-based dry powder composition that comprises spray-drying an aqueous mixture of the interferon and the carrier under conditions to provide a respirable dry powder.

DESCRIPTION OF SPECIFIC EMBODIMENTS

The present invention is based at least in part on the higher potency and improved flow characteristics of interferon-based dry powder compositions produced by spray drying according to the present invention. Higher potency means that the resulting interferon-based composition has a higher percentage of physiologically active interferon than compositions prepared by other methods. The compositions of the invention are readily aerosolized and rapidly absorbed through the lungs of a host when delivered by a dry powder inhaler.

Definitions

In interpreting the claims to the various aspects of this invention, there are several important definitions that should be considered.

The term "interferon" is meant to include the family of naturally-occurring or recombinantly prepared small proteins and glycoproteins (sometimes referred to as cytokines) with molecular weight between approximately 15,000 and 27,000 daltons and having interferon-like activity. Generally, such activity is exerted by binding to specific membrane receptors on a cell surface. Once bound, interferons initiate a complex series of intracellular events that vary among the various interferons. Interferons are useful in the treatment of a variety of human conditions varying from cancer to immune system suppression. Naturally occurring interferons are produced and secreted by cells in response to viral infections and to synthetic and biological inducers. Some interferons are modified versions of the naturally occurring material and are prepared using recombinant DNA technology. Interferon is sometimes abbreviated as "IFN" and shall be so abbreviated in this application. Examples of interferons include, e.g. IFN-alpha-2A recombinant (Roferon® A-Roche Laboratories), IFN-alpha-2B recombinant (Intron® A-Shering), IFN-alpha-N3 human leukocyte derived (Alferon® N-Purdue Frederick), IFN-gamma-1B (Actimmune®-Genentech), IFN-beta recombinant (Betaseron®-Chiron, Berlex), IFN-beta naturally occurring (Feron®-Toray, Japan), and the like. U.S. Pat. No. 4,503,035 issued Mar. 5, 1985 to Pestka and Rubinstein gives examples of human leukocyte IFNs. For purposes of this invention IFN-beta is preferred, particularly naturally occurring IFN-beta.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 microns ($\mu$m) in diameter with a relatively uniform spheroidal shape distribution. More preferably the diameter is less than about 7.5 $\mu$m and most preferably less than about 5.0 $\mu$m. Usually the particle size distribution is between about 0.1 $\mu$m and about 5 $\mu$m in diameter, particularly about 2 $\mu$m to about 5 $\mu$m.

The term "dry" means that the composition has a moisture content such that the particles are readily dispersable in an inhalation device to form an aerosol. This moisture content is generally below about 10% by weight (% w) water, usually below about 5% w and preferably less than about 3% w.

The term "therapeutically effective amount" is the amount present in the composition that is needed to provide the desired level of interferon in the subject to be treated to give the anticipated physiological response. This amount is determined for each interferon on a case-by-case basis. Guidelines are given hereafter.

The term "physiologically effective amount" is that amount delivered to a subject to give the desired palliative or curative effect. This amount is specific for each interferon and its ultimate approved dosage level. Guidelines are given hereafter.

The term "pharmaceutically acceptable" carrier means that the carrier can be taken into the lungs with no significant adverse toxicological effects on the lungs.

Compositions of the Invention

One aspect of this invention is an interferon-based dry powder composition for pulmonary delivery, the composition comprising a therapeutically effective amount of interferon in combination with a pharmaceutically acceptable carrier.

In general, the compositions of this invention have a higher IFN potency and greater dispersibility than other interferon compositions known in the art. In the dry state IFN is an amorphous form. The IFNs suitable for use in the composition of this invention include the various IFN alphas, IFN betas and IFN gammas encompassed by the broad definition of IFN. The IFN alphas and IFN betas are preferred, with IFN beta being particularly preferred. The composition is particularly valuable for naturally occurring IFN beta, for example that available through Toray Industries, Inc. in Japan.

A therapeutically effective amount of IFN will vary in the composition depending on the biological activity of the IFN employed and the amount needed in a unit dosage form. Because IFN is so highly active it must be manufactured in a unit basis in a manner that allows for ready manipulation by the formulator and by the consumer. This generally means that a unit dosage will be between about 0.5 mg and 15 mg of total material in the dry powder composition, preferably between about 2 mg and 10 mg. Generally, the amount of IFN in the composition will vary from about 0.05% w to about 5.0% w. Most preferably the composition will be about 0.2% to about 2.0% w IFN.

The amount of the pharmaceutically acceptable carrier is that amount needed to provide the necessary stability, dispersibility, consistency and bulking characteristics to ensure a uniform pulmonary delivery of the composition to a subject in need thereof. Numerically the amount may be from about 95.0% w to about 99.95% w, depending on the activity of the IFN being employed. Preferably about 98% w to about 99.8% w will be used.

The carrier may be one or a combination of two or more pharmaceutical excipients, but will generally be substantially free of any "penetration enhancers." "Penetration enhancers" are surface active compounds which promote penetration of a drug through a mucosal membrane or lining and are proposed for use in intranasal, intrarectal, and intravaginal drug formulations. Exemplary penetration enhancers include bile salts, e.g., taurocholate, glycocholate, and deoxycholate; fusidates, e.g., taurodehydrofusidate; and biocompatible detergents, e.g., Tweens, Laureth-9, and the like. The use of penetration enhancers in formulations for the lungs, however, is generally undesirable because of the epithelial blood barrier in the lung can be adversely affected by such surface active compounds. The dry powder compositions of the present invention are readily absorbed in the lungs without the need to employ penetration enhancers.

The types of pharmaceutical excipients that are useful as carriers in this invention include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

It has been found that HSA is particularly valuable as a carrier in that it provides excellent stabilization of IFN in solution.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-$\beta$-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Additives, which are minor components of the composition of this invention, may be included for conformational stability during spray drying and for improving dispersibility of the powder. These additives include hydrophobic amino acids such as tryptophan, tyrosine, leucine, phenylalanine, and the like.

Suitable pH adjusters or buffers include organic salts prepared from organic acids and bases, such as sodium citrate, sodium ascorbate, and the like; sodium citrate is preferred.

The unit dosage form, method of treatment, and process of preparation of this invention are described hereafter.

Unit Dosage Form

Another aspect of this invention is a unit dosage form for pulmonary delivery of interferon, which dosage form comprises a unit dosage receptacle containing an interferon-based dry powder composition, which composition comprises a therapeutically effective amount of an interferon in combination with a pharmaceutically acceptable carrier.

In this aspect of the invention, the composition of this invention (as discussed hereinbefore) is placed within a suitable dosage receptacle in an amount sufficient to provide a subject with IFN for a unit dosage treatment. The dosage receptacle is one that fits within a suitable inhalation device to allow for the aerosolization of the interferon-based dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522 issued Oct. 14, 1980; U.S. Pat. No. 4,192,309 issued Mar. 11, 1980; and U.S. Pat. No. 4,105,027 issued Aug. 8, 1978. Suitable containers also include those used in conjunction with Glaxo's Ventolin Rotohaler brand powder inhaler or Fison's Spinhaler brand powder inhaler. Another suitable unit-dose container which provides a superior moisture barrier is formed from an aluminum foil plastic laminate. The IFN-beta powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference.

Method of Treating a Disease State

Another aspect of this invention is a method of treating a condition responsive to treatment by interferon, which method comprises pulmonarily administering to a subject in need thereof a physiologically effective amount of an interferon-based dry powder composition that comprises a therapeutically effective amount of an interferon in combination with a pharmaceutically acceptable carrier.

Conditions that may be treated by the composition of this invention include those conditions that are responsive generally to treatment with IFN. For example, IFN alpha is used to treat hepatitis B and C, Hairy Cell Leukemia, chronic hepatitis Non A, Non B/C and Kaposi's Sarcoma; IFN beta is used to treat multiple sclerosis, brain tumor, skin cancer and hepatitis B and C; and IFN gamma is used to treat chronic granulomatous disease.

The physiologically effective amount needed to treat a particular condition or disease state will depend on the individual, the condition, length of treatment, the regularity of treatment, the type of IFN, and other factors, but can be determined by one of ordinary skill in the medicinal arts. The dosage may range from $0.25 \times 10^6$ IU to $50 \times 10^6$ IU per person per day depending on the prescribing doctor's diagnosis. For example an induction dosage of IFN alpha recombinant (Roferon® A-Roche Laboratories) for treatment of hairy cell leukemia may be $3 \times 10^6$ IU daily for 16–24 weeks with a maintenance dose of $3 \times 10^6$ IU three times per week. Other dosage regimes may be determined through clinical trials and reference to the Physicians Desk Reference® for 1994 as supplemented.

It is presently believed that the effective absorption by a host of dry powder interferon according to the present invention results from a rapid dissolution in the ultra-thin (<0.1 fm) fluid layer of the alveolar lining of the lung. The particles of the present invention thus have a mean size which is from 10 to 50 times larger than the lung fluid layer, making it unexpected that the particles are dissolved and the interferon systemically absorbed in a rapid manner for either local lung or systemic treatment. An understanding of the precise mechanism, however, is not necessary for practicing the present invention as described herein.

The aerosolized interferon-based dry powders of this invention are particularly useful in place of parenteral delivery. Thus, the methods and compositions of the present invention will be particularly valuable in chronic treatment protocols where a patient can self-medicate. The patient can achieve a desired dosage by inhaling an appropriate amount of interferon, as just described. The efficiency of systemic interferon delivery via the method as just described will typically be in the range from about 15% to 50%, with individual dosages (on a per inhalation basis), typically being in the range from about 3 million IU to about 50 million IU during a single respiratory administration. Thus, the desired dosage may be effected by the patient taking from 1 breath to 5 breaths.

Method for Aerosolizing the Powder

Still another aspect of this invention is a method for aerosolizing an interferon-based dry powder composition that comprises a therapeutically effective amount of an interferon in combination with a pharmaceutically acceptable carrier, which method comprises dispersing an amount of the dry powder composition in a gas stream to form an aerosol and capturing the aerosol in a chamber having a mouthpiece for subsequent inhalation by a patient.

A further detailed description of this method is found in pending U.S. patent applications Ser. Nos. 07/910,048 and 08/207,472, both of which are incorporated herein by reference.

Preparing the Compositions

Still another aspect of this invention is a method for preparing an interferon-based dry powder composition of this invention that comprises spray-drying an aqueous mixture of the interferon and a pharmaceutically acceptable carrier having an interferon-stabilizing pH under conditions to provide a respirable dry powder composition.

Spray drying is a process in which a homogeneous aqueous mixture of IFN and the carrier is introduced via a nozzle (e.g., a two fluid nozzle), spinning disc or an equivalent device into a hot gas stream to atomize the solution to form fine droplets. The aqueous mixture may be a solution, suspension, slurry, or the like, but needs to be homogeneous to ensure uniform distribution of the components in the mixture and ultimately the powdered composition. Preferably the aqueous mixture is a solution. The solvent, generally water, rapidly evaporates from the droplets producing a fine dry powder having particles 1 to 5 μm in diameter. Surprisingly, the protein is not degraded when it is exposed to the hot drying gas, and the interferon powders can be prepared having sufficient purity for pharmaceutical use. An acceptable purity is defined as less than 5% degradation products and contaminates, preferably less than 3% and most preferably less than 1%.

The spray drying is done under conditions that result in substantially amorphous powder of homogeneous constitution having a particle size that is respirable, a low moisture content and flow characteristics that allow for ready aerosolization. Preferably the particle size of the resulting powder is such that more than about 98% of the mass is in particles having a diameter of about 10 μm or less with about 90% of the mass being in particles having a diameter less than 5 μm. Alternatively, about 95% (preferably more than 95%) of the mass will have particles with a diameter of less than 10 μm with about 80% (preferably more than 80%) of the mass of the particles having a diameter of less than 5 μm.

According to the methods of the present invention, interferon dry powders of higher potency and improved flow characteristics are prepared by spray drying, where, bulk interferon, preferably IFN-beta but suitably other forms of interferon, is prepared in solution to have a concentration from 0.0005% by weight to 0.02% by weight, usually from 0.001% to 0.005%. The solutions may contain a stabilizer to maintain the chemical stability of the IFN-beta in solution such as HSA in a concentration from 0.01% to 1.0% by weight and preferably 0.05% to 0.25% by weight and may contain other material such as a salt or preservative that is present as a result of the preparation of bulk IFN. The solutions may then be sprayed dried in conventional spray drying equipment from commercial suppliers, such as Buchi, Niro, Yamato Chemical Co., Okawara Kakoki Co., and the like, resulting in a substantially amorphous particulate product.

For the spraying process, such spraying methods as rotary atomization, pressure atomization and two-fluid atomization can be used. Examples of the devices used in these processes include "Pulvis Mini-Spray GA-32" and "Pulvis Spray Drier DL-41", manufactured by Yamato Chemical Co., or "Spray Drier CL-8.' "Spray Drier L-8," "Spray Drier FL-12," "Spray Drier FL-16" or "Spray Drier FL-20," manufactured by Okawara Kakoki Co., can be used for the method of spraying using rotary-disk atomizer.

While no special restrictions are placed on the nozzle of the atomizer used in the process of spraying, it is recommended to use a nozzle which can produce a spray-dry composition with a grain diameter suitable for nasal, pharyngeal or pulmonary administration. For example, nozzle types "1A," "1," "2A," "2," "3" and the like, manufactured by Yamato Chemical Co., can be used for the above-mentioned spray-drier, manufactured by the same company. In addition, disks type "MC-50," "MC-65" or "MC-85," manufactured by Okawara Kakoki Co., can be used as rotary disks of the spray-drier atomizer, manufactured by the same company.

While no particular restrictions are placed on the gas used to dry the sprayed material, it is recommended to use air, nitrogen gas or an inert gas. The temperature of the inlet of the gas used to dry the sprayed materials such that it does not cause heat deactivation of the sprayed material. The range of temperatures may vary between about 50° C. to about 200° C., preferable between about 50° C. and 100° C. The temperature of the outlet gas used to dry the sprayed material, may vary between about 0° C. and about 150°, preferably between 0° C. and 90° C., and even more preferably between 0° C. and 60° C. The fact that inlet and outlet temperatures above about 55° C. can be used is surprising in view of the fact that IFN starts deactivating at that temperature, with nearly complete deactivation occurring at about 70° C.

By minimizing the amount of stabilizer in the solution, high potency IFN powder can be prepared such that the number of inhalations required to deliver even high dosages of IFN can be substantially reduced, often to only a single inhalation.

Interferon dry powders suitable for use in the present invention are substantially amorphous, essentially lacking any crystalline structure. Dry powder interferons are prepared by spray drying under conditions which result in a substantially amorphous powder having a particle size within the above-stated range. According to the method of the present invention, bulk interferon, preferably IFN-β but suitably other forms of interferon, is first dissolved in a physiologically-acceptable aqueous solution typically containing sodium chloride, optionally with a buffer, having a pH in the range from about 2 to 9. The interferon is dissolved at a concentration from 0.01% by weight to 1% by weight, usually from 0.1% to 0.2%. The solutions may then be spray dried in conventional spray drying equipment from commercial suppliers, such as Buchi, Niro Yamato, Okawara Kakoki and the like, resulting in a substantially amorphous particulate product.

The interferon dry powders of the present invention may optionally be combined with pharmaceutical carriers or excipients which are suitable for respiratory and pulmonary administration. Such carriers may serve simply as bulking agents when it is desired to reduce the interferon concentration in the powder which is being delivered to a patient, but may also serve to enhance the stability of the interferon compositions and to improve the dispersibility of the powder within a powder dispersion device in order to provide more efficient and reproducible delivery of the interferon and to improve handling characteristics of the interferon such as flowability and consistency to facilitate manufacturing and powder filling.

Such carrier materials may be combined with the interferon prior to spray drying, i.e., by adding the carrier material to the purified bulk solution. In that way, the carrier particles will be formed simultaneously with the IFN particles to produce a homogeneous powder. Alternatively, the carriers may be separately prepared in a dry powder form and combined with the dry powder interferon by blending. The powder carriers will usually be crystalline (to avoid water absorption), but might in some cases be amorphous or mixtures of crystalline and amorphous. The size of the carrier particles may be selected to improve the flowability of the IFN powder, typically being in the range from 25 μm to 100 μm. A preferred carrier material is crystalline lactose having a size in the above-stated range.

Experimental

EXAMPLE I

This example sets forth a method of preparing a composition of this invention.

Approximately 50 mL of 10 mM sodium chloride solution of natural human IFN-beta comprising approximately 2 mg/ml HSA was prepared.

The resulting aqueous mixture is fed to a Buchi Laboratory Spray Dryer under the following conditions to give a composition of this invention:

| | |
|---|---|
| Temperature of the aqueous mixture | 4° C.–10° C. |
| Inlet temperature | 115° C.–125° C. |
| Feed rate | 6 mL/min |
| Outlet temperature | 60° C.–70° C. |

Once the aqueous mixture is consumed, the outlet temperature is maintained at about 70° C. for about 15 minutes by slowly decreasing the inlet temperature. This provides a secondary drying to give an IFN-based dry powder composition having a water content of less than 3% as measured by a coulombic Karl Fischer method. In this case the composition (% w based on total solids) is constituted as follows:

| | |
|---|---|
| 1.9% w | IFN-beta |
| 98.1% w | Carrier (75.8% HSA, 22.3 NaCl) |

EXAMPLE II

By following the procedure of Example I, but increasing the outlet temperature to 75° C.–80° C. during the secondary drying stage, one obtains a composition of this invention having less than 1% w water.

EXAMPLE III

This example sets forth a method of preparing a composition of this invention wherein the carrier includes a bulking agent, i.e., mannitol.

Mannitol is dissolved in natural human IFN-beta described in Example I. The concentration of mannitol was 5.75 mg/mL.

The resulting aqueous mixture is fed to a Buchi Laboratory Spray Dryer under the following conditions:

| | |
|---|---|
| Temperature of the aqueous mixture | 4° C.–10° C. |
| Inlet temperature | 115° C.–125° C. |
| Feed rate | 5 mL/min |
| Outlet temperature | 60° C.–70° C. |
| Secondary drying- 15 minutes at | 70° C. |

Although the foregoing invention has been described in some detail by way of illustration and example, for purposes of clarity of understanding, it will be obvious that certain changes and modifications may be practiced within the scope of the appended claims.

EXAMPLE IV

This example sets forth a method for preparing a composition of this invention wherein no bulking agent is present in the composition.

Approximately 100 ml of 10 mM sodium chloride solution of natural human interferon (obtained by culturing human normal diploid fibroblasts) (approximately 7×10$^4$ IU/ml) comprising approximately 2 mg/ml human serum albumin (HSA) were prepared, and spray-dried using the commercial spray-drier "Pulvis Mini-Spray GA-32," manufactured by Yamato Chemical Co. The spray nozzle used was a 1A nozzle (Φ0.4 mm) and the inlet temperature and the outlet temperature of the drying gas were 100° C. and 60° C., respectively. In addition, the spray pressure was 1 kg/cm$^2$, the flow capacity of the hot air was 0.40 to 0.42 m$^3$/min and the rate of solution transmission was 4.3 ml/min. After approximately 20 min. of spray-drying, the dry powder, which was collected into a chamber using a cyclone, was recovered, and the interferon (IFN) activity was measured. The interferon activity was measured using an enzyme immunoassay (EIA) involving an anti-human interferon β antibody (S. Yamazaki et al., *Immunoassay*, 10, 57(1989)). The activity of the dry powder was measured by dissolving the dry powder using distilled water and comparing its interferon activity, corresponding to the light absorption at 280 nm, with the interferon activity prior to the spray-drying process. The results are shown in Table 1. The measurements were repeated three times, and the average values were used for the comparison. The error in the relative activity in the table is a standard error (±SE).

TABLE 1

Natural human interferon β activity before and after spray-drying

| | Relative activity (IU/A 280 unit) | Remaining activity (%) |
|---|---|---|
| Before spray-drying | 4.11 ± 0.11 | 100 |
| After spray-drying | 3.14 ± 0.04 | 74.8 |

After the spray-drying process, the natural human interferon β showed an interferon activity which was 74.8% of its activity prior to the spray-drying process, indicating that it can be spray-dried while maintaining its activity. These results are surprising because a similar natural human interferon β solution comprising a similar quantity of HSA will start deactivating at approximately 55° C., with complete deactivation occuring at 70° C.

The dry powder obtained by the process of this invention was subjected to platinum coating and the shape of its grains was examined using a field emission scan electron microscope (model S-8000, manufactured by Hitachi Co.). Approximately 90% of the grains examined were grains with relatively smooth and large dents and protrusions in the grain surface, and with a grain diameter of approximately 10 μm. In addition, the resulting powder exhibited a moisture content of 5.6 wt % using the Karl Fischer method (coulometric titration Moisturemeter CA-06, manufactured by Mitsubishi Kasei Co.).

EXAMPLE V

This example sets forth a method for preparing an IFN/HSA/mannitol composition.

Approximately 100 ml of 10 mM sodium chloride solution of natural human interferon comprising 150 mg/ml mannitol and approximately 2 mg/ml human serum albumin (HSA) were prepared. The proportion of the mannitol to the total solutes in this solution composition was approximately 90 wt %.

The above solution was spray-dried using the same method and the same conditions as in Example IV, and the interferon activity of the dry powder obtained was measured using the same method as in Example IV. The results are shown in Table 2.

TABLE 2

Natural human interferon β activity before and after spray-drying

| | Relative activity (IU/A 280 unit) | Remaining activity (%) |
|---|---|---|
| Before spray-drying | 5.59 ± 0.51 | 100 |
| After spray-drying | 4.53 ± 0.13 | 81.0 |

After the spray-drying process, the natural human interferon β maintained 81.0% of its activity compared with its activity prior to the spray-drying process. As in Example IV, these results are surprising because a similar aqueous solution of the same quantity of natural human interferon β, HSA and mannitol started to deactivate at approximately 55° C., with almost complete deactivation occurring at 70° C.

While the IFN-based powder from Example IV and V are dispersible, the powder obtained from Example V was more readily dispersed than the powder obtained in Example IV.

When the grain shape was examined by subjecting the powder to platinum coating and using a field emission scan electron microscope (model S-8000, manufactured by Hitachi Co.), the grains were found to have a size similar to those of Example IV but a shape more rounded compared with the powder particles obtained in Example IV. In addition, when the distribution of the grain diameter of the powder was measured by dispersing it in ethanol anhydride and using a granulation analyzer (Microtrac FRA, manufactured by Nikkiso Co.), it was found that approximately 90% of the grains were distributed within the range of 1.6 to 9.3 μm. The moisture content was 0.74% wt, as measured by the Karl Fischer method of Example IV.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

The subject matter claimed is:

1. A dispersible dry powder for pulmonary delivery, comprising a therapeutically effective amount of an interferon in combination with a hydrophobic amino acid.

2. A spray-dried powder of claim 1.

3. The dry powder of claim 1, wherein said amino acid is selected from the group consisting of tryptophan, tyrosine, leucine, and phenylalanine.

4. The dry powder of claim 1, further comprising a pharmaceutically acceptable carrier.

5. The dry powder of claim 1, wherein about 95% of the mass of the dry powder has a particle size of less than 10 μm.

6. The dry powder of claim 1, wherein about 80% of the mass of the dry powder has a particle size of less than 5 μm.

7. The dry powder of claim 1, wherein the interferon is naturally-occurring.

8. The dry powder of claim 1, wherein the interferon is interferon-beta.

9. The dry powder of claim 1, having a moisture content of less than about 5%.

10. A unit dosage form for pulmonary delivery of interferon comprising a unit dosage receptacle containing the dry powder of any one of claims 1–6.

11. The dry powder of claim 3, wherein said amino acid is leucine.

12. The dry powder of claim 4, wherein said carrier comprises a carbohydrate bulking agent.

13. The dry powder of claim 12, wherein said carbohydrate is selected from the group consisting of lactose, trehalose, raffinose, maltodextrins, and mannitol.

14. A method for treating a disease state responsive to treatment by an interferon, comprising pulmonarily administering to a subject in need thereof a physiologically effective amount of a disperisible dry powder comprising a therapeutically effective amount of an interferon in combination with a hydrophobic amino acid.

15. The method of claim 14, wherein said powder is spray-dried.

16. The method of claim 14, wherein said hydrophobic amino acid is selected from the group consisting of tryptophan, tyrosine, leucine, and phenylalanine.

17. The method of claim 14, wherein said powder further comprises a pharmaceutically acceptable carrier.

18. The method of claim 16, wherein said hydrophobic amino acid is leucine.

19. A method for aerosolizing an interferon-containing dry powder, said method comprising:
    dispersing an amount of the dry powder of any one of claims 1–6 in a gas stream to form an aerosol, and
    capturing the aerosol in a chamber for subsequent inhalation by a patient.

20. A method for preparing an interferon-based dry powder suitable for pulmonary delivery, said method comprising:
    spray-drying an aqueous mixture of an interferon and a hydrophobic amino acid under conditions effective to provide a respirable powder.

21. The method of claim 20, wherein the spray-dried powder is substantially amorphous.

22. The method of claim 20, wherein the interferon in the spray-dried powder maintains at least about 75% of its initial activity.

* * * * *